United States Patent [19]

LaFleur

[11] Patent Number: 4,610,680
[45] Date of Patent: Sep. 9, 1986

[54] DISPOSABLE TRAINING PANTY

[76] Inventor: Ruby S. LaFleur, 10490 W. Outer Dr., Detroit, Mich. 48223

[21] Appl. No.: 728,109

[22] Filed: Apr. 29, 1985

[51] Int. Cl.⁴ .............................................. A61F 13/16
[52] U.S. Cl. .................................................. 604/385 A
[58] Field of Search ................ 604/385, 358, 396, 394

[56] References Cited

U.S. PATENT DOCUMENTS 2,834,347  5/1958  Connally ............................. 604/385
3,407,813  10/1968  Grippo et al. ...................... 604/385
4,145,763  3/1979  Abrams et al. .................. 604/385 X Primary Examiner—John D. Yasko
Attorney, Agent, or Firm—Gifford, Groh, VanOphem, Sheridan, Sprinkle & Dolgorukov

[57] ABSTRACT

A disposable training panty comprises a panty member adapted to form an enclosed waist opening and enclosed leg openings from a panel having an inner layer of absorbant material and an outer layer of water impervious material. Preferably the openings are peripherally defined at least in part by elastic material. In an advantageous form of the invention, portions of the panty member can be separated from each other to open the periphery of waist opening of the panty member and the leg openings. In one form of the invention a strand is secured to the panty member along predetermined lines so that pulling of the strand tears the panty member between the leg openings and between the waist band and at least one leg opening. In another form of the invention, the panty member includes overlapping flaps which can be secured to each other by hook and pile fastening straps. Alternatively, the overlapping flaps or the strands can extend along the sides of the panty member between the waist band and each leg band.

17 Claims, 6 Drawing Figures

DISPOSABLE TRAINING PANTY

BACKGROUND OF THE INVENTION

I. Field of the Invention

The present invention relates generally to training panties for very young children learning to control urination, and more particularly to such panties having means for dissembling the panty member so that it can be removed from the child's body and disposed of without manipulation of the child's body therethrough.

II. Description of the Prior Art

A problem with uncontrolled urination and bowel movements is that a panty garment can become extremely soiled. In order to avoid frequent laundering and the inability to remove extremely set stains, disposable diapers have been made available. Such diapers comprise a garment flap, usually formed of layers of material, having a tab on each side at one end adapted to overlap and adhesively engage the other end of the flap when it has been wrapped over a child's body. Such diapers often include an absorbant inner layer and an outer layer of plastic or other nonporous material which prevents leakage to the outer garments. However, while such garments are likely to remain assembled when applied to the body of a fairly small infant, such garments are not well adapted for use by more active children with slightly greater maturity who are in the process of learning to control urination.

Moreover, although typical undergarments having a waist band and a pair of leg bands to form a substantially unitary garment which does not become undone during activities are already known, such garments can be difficult to remove. In particular, once a garment has become soiled, removal of the garment can substantially increase the spread of soilage, especially since the garment must be pulled over the child's legs.

A modified form of disposable training panties is disclosed in my previous U.S. Pat. No. 4,280,230 in which a disposable crotch member is removable from the main portion of the garment containing the waist band the leg band. However, while a removable crotch member substantially eases the ability to clean up the child and remove the soilage, it can be appreciated that the area of soilage is not limited only to the crotch area. As a result, the problem of removal of the entire garment and its soilage spreading problem can still be encountered with such a garment. Moreover, while the patent also suggests that the crotch can be torn open, such tearing does not provide complete removal of garment from the baby without further manipulating portions such as the waist band of the garment over the child's body.

SUMMARY OF THE PRESENT INVENTION

The present invention overcomes the above-mentioned disadvantages by providing a disposable training panty having an inner absorbant layer, an outer impervious layer, and elastic band portions. In one advantageous form of the invention, portions of the garment can be bifurcated to completely remove the garment from the body without manipulation of the body through the openings in the garment. In the preferred embodiment, the garment can be formed substantially in a single piece, in the manner of previously known undergarments, and has a tearing strand secured to the garment so as to bifurcate it in at least two places. Alternatively, the garment can be formed from overlapping panels and the overlapping portions of the panels can be releasably engaged to permit the garment to open in at least two positions. Preferably, the garment includes an outer layer of nonporous material and an inner layer of absorbant material. Preferably, the absorbant material is paper.

As a result, the present invention provides a garment which can be worn by an active child without inadvertent mispositioning or disassembly during a child's activity. Nevertheless, the garment is easily removed from the child, and can be easily adapted for removal without manipulating the child's body through the waist and leg openings and further spreading the soilage. Moreover, the garment can be made resealable so that the garment can be worn again if it has been removed to check for soilage.

BRIEF DESCRIPTION OF THE DRAWING

Although the garment will be described throughout this application with reference to use by a child it should be understood that it can be used by adults as well in those situations when for health or other reasons such a garment would be worn by an adult.

The present invention will be more clearly understood by reference to the following detailed description of a preferred embodiment when read in conjunction with the accompanying drawing in which like reference characters refer to like parts throughout the views and in which.

DETAILED DESCRIPTION OF A PREFERRED EMBODIMENT OF THE PRESENT INVENTION

Figure 1:
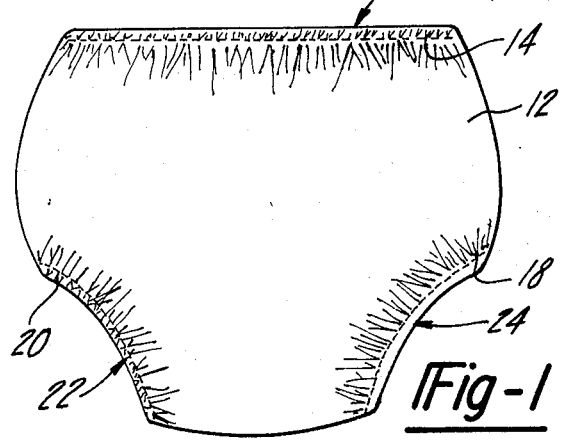
FIG. 1 is a front view of a disposable training panty according to the present invention.

Referring first to FIG. 1, a disposable training panty 10 according to the present invention is thereshown comprising a substantially one-piece, two layer panty member 12 having a waist band 14 peripherally defining a waist opening 16. In addition, the panty member 12 includes leg bands 18 and 20 defining leg openings 22 and 24 respectively. The garment 10 is completely closed except at the defined openings. While the bands 14, 18 and 20 are shown in FIG. 1 in the form of hems, as will be described in greater detail hereinafter, it is to be understood that the term band is not intended to be limited to a particular garment construction. Rather, the term is to be understood as referring to any continuous edge defining the periphery of an opening through the panty garment. Moreover, the term is intended to include the peripheral edges of panties formed from separate pieces which are stitched or otherwise secured together to form a continuous periphery around a waist opening or leg opening in a panty.

Figure 4:
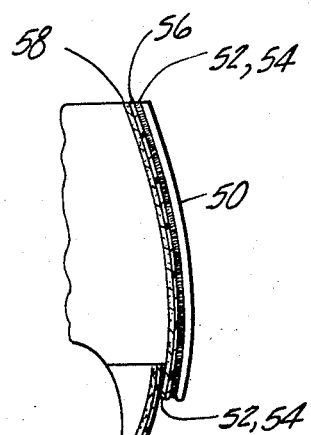
FIG. 4 is a broken sectional view taken substantially along the line 4—4 in FIG. 3

The panel 12 comprises an inner layer of cotton, paper or other absorbant combinations of materials which can collect uncontrolled urination. The outer layer is made of water impervious material, such as a thin plastic, to prevent soilage of any outer garments. As best shown in FIG. 4, the double layer construction of the panel 12 is applicable to all garments constructed in accordance with the present invention.

In the garment 10 shown in FIG. 1, the waist band 14 includes elastic portions 26 which permit the band 14 to tightly engage the torso of the child. Similarly, the leg bands 18 and 20 include elastic portions 28 to tightly enclose panty 10 around the legs of a child. The elastic portions 28 are separated by a flat portion 30. Of course, the entire band can be constructed of elastic material if desired.

Figure 2:
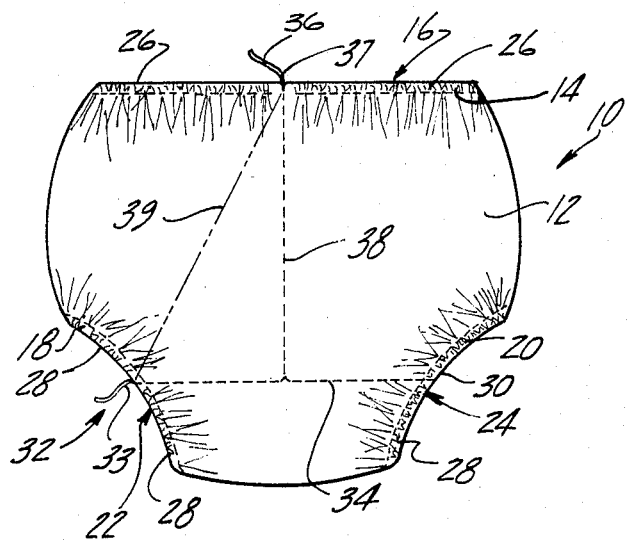
FIG. 2 is a front view similar to FIG. 1 but showing a modification of the disposable panty according to the present invention.

Referring now to FIG. 2, a tear strand 32 extends across the flat band portions 30. The strand 32 is secured to the material forming the bands 18 and 20 as well as the member 12 substantially along the entire length of the strand 32 but the strand is slightly longer than the distance between the bands 18 and 20 so that a free end 33 extends beyond an edge of the garment. The strand 32 is formed of a material having greater cohesive strength than the material forming the bands 18 and 20 and panel 12 and is stitched to the inner surface of the member 12 or otherwise secured to the member 12. As a result, the free end 33 of strand 32 can be pulled to tear the material forming the bands 18 and 20 and the panty member 12 therebetween, thereby bifurcating the panel along a line 34 extending between the leg openings 22 and 24.

In a similar manner, a substantially similar strand 36 is secured to the panty member 12 across the waist band 14 along the line 38 extending toward the line 34 formed by strand 32. The strand 36 is stitched or otherwise secured to the panty member 12 along its length so that an end portion 37 extends beyond the waist band 14. Preferably, the strand 36 is aligned with a flat portion 40 of the waist band 14 in between elastic portions 26. Alternatively, strand 36 can be secured to extend across the waist band 14 along the line 39 from the flat area 30 to one of the leg bands 18 and 20.

It will be understood that once the panty 10 has been worn, the strands 32 and 36 can be pulled to tear the panty member 12 across the lines 34 and 38 to bifurcate the panel in two directions. As a result, the panel 12 is bifurcated along the two lines and completely opened for easy removal from the child's body without manipulating the body through the previously enclosed waist and leg openings. Bifurcating the garment along line 38 or line 39 is equally effective in opening the garment for removal from the child's body.

Figure 3:
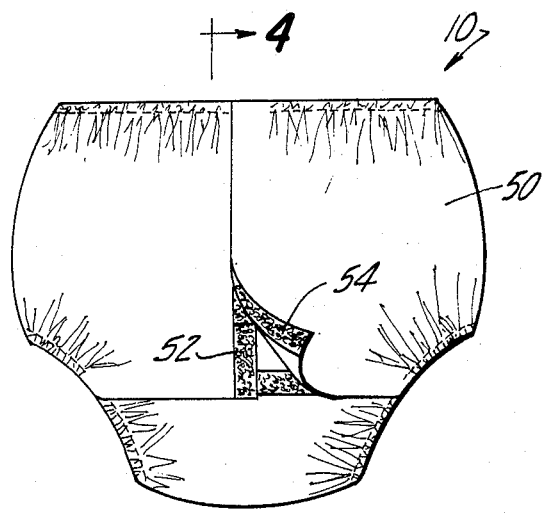
FIG. 3 is a front view similar to FIG. 2 but showing a modification of the disposable panty according to the present invention.

Referring now to FIG. 3, a resealable garment 10 according to the present invention is formed from a panty member 50 having overlapping flap portions which can be sealed to form a completely enclosed waist band 14 and the leg bands 18 and 20. In the preferred embodiment, the overlapping flap portions of a member 50 are connected by mating, hook and pile fastening strips, such as velcro fastening strips, aligned substantially along the lines 34 and 38, or 34 and 39, as shown in FIG. 2. The fastening strips 52 and 54 provide secure attachment of the overlapping edges of the panty member 50, whereby the waist opening 16 and leg openings 22 and 24 remain completely enclosed while the garment is being worn. Nevertheless, disengagement of the strips 54 from the strips 52 enables the panty 10 to be bifurcated substantially along the lines 34 and 38 shown in FIG. 2 so that the garment can be completely unwrapped from the child's body without manipulation of the child's body through the panty openings.

Referring to FIG. 4, the hook and pile fastening strips 52 and 54 are shown mated together to form a single adhesive layer. As is also shown in FIG. 4, panty member 50 comprises an outer layer of plastic material 56 to prevent the seepage of soilage therethrough. An inner layer 58, preferably made of paper, absorbs any moisture which is released within the panty 10. The edges of the separated panels of member 50 which form the overlapping flaps can be folded over and sewn in the form of a hem to provide a finished appearance to the edges in much the same manner as the waist band 14 and leg bands 18 and 20 are formed. It is also to be understood that the panty 10 shown in FIGS. 1 and 2, and the panties 110 shown in FIGS. 5 and 6 can also be made with similar layers and hems.

Figure 5:
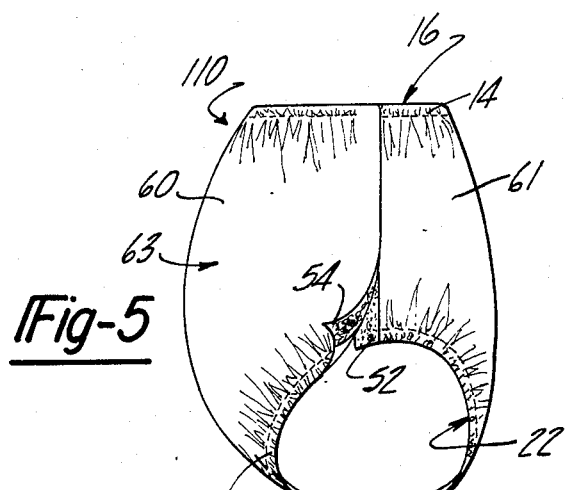
FIG. 5 is a side view of a disposable training panty showing a further modification.

Referring now to FIG. 5, a disposable training panty 110 according to the present invention is thereshown formed from a panty member 60 having overlapping flap portions extending across the waist band 14, the member 60 and the leg band 18. A similar set of overlapping flaps extends along the opposite side of the panty 10 from the waist band 14 to the leg band 24. The overlapping flap portions are sealed together by mating, hook and pile, fastening strips 52 and 54 as previously discussed with respect to FIGS. 3 and 4. As a result, the entire front flap portion 61 of the garment member 60 can be detached from the rear flap portion 63 of the garment member 60 at each side in order to remove the garment when desired.

Figure 6:
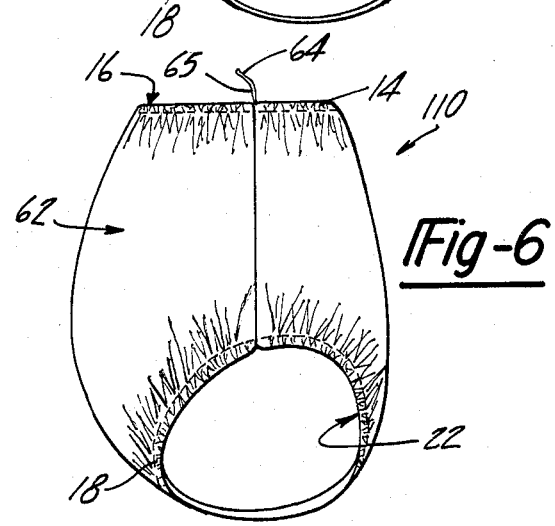
FIG. 6 is a side view similar to FIG. 5 but showing still further modification of the disposable training panty.

The panty 110 shown in FIG. 6 comprises a panty member 62 substantially the same as the panel member 12 shown in FIG. 1. However, a strand 64 secured along each side of the panty 110 across the waist band 14, panel 62 and the respective leg band 18 or 20. The strand 64 is slightly longer than the length of the panel 62 between the waist opening 16 and the respective leg opening 22 or 24 so that a free end 65 extends outwardly from one end and can be grasped. Thus, the strands 64 can be pulled to tear the garment across the waist band 14, the member 62 and the leg bands 18 or 20, respectively, to separate the front half of the garment 110 from the rear half for removal of the garment from the child's body without manipulating the body through an enclosed waist opening 16 or enclosed leg openings 22 and 24.

Having thus described my invention, many modifications thereto will become apparent to those skilled in the art to which it pertains without departing from the scope and spirit of the present invention as defined in the appended claims.

What is claimed is:

1. A training panty comprising:
   a panty member having a waist band defining a waist opening and two leg bands defining two spaced apart leg openings separated by an intermediate portion of said member, said panty member being formed with an outer layer of material substantially impervious to water, and an inner layer of water absorbant material, and
   means for selectively splitting said member, said waist band and both said leg bands, said means including means for bifurcating the intermediate portion of said member along a first line extending from one leg opening to the other leg opening and means for bifurcating said panty member along a second line extending inclusively from said waist band to one of said first line and said leg opening.

2. The invention as defined in claim 1 wherein said bifurcating means comprises at least one first flap portion, at least one second flap portion and means for detachably securing said at least one first flap portion to said at least one second flap portion.

3. The invention as defined in claim 1 wherein said bifurcating means comprises at least one first flap portion, at least one second flap portion and means for detachably securing said at least one first flap portion to said at least one second flap portion, and wherein said at least one first flap portion overlaps said at least one second portion along said second line and further comprising at least one third flap portion and means for detachably securing said third flap portion to each of said first and second flap portions along said first line.

4. The invention as defined in claim 1 wherein each said bifurcating means comprises a strand having greater cohesive strength than said member, said waist band and said leg bands, and means for substantially coextensively securing said strand to said panel member said waist band and said leg band.

5. The invention as defined in claim 1 wherein said waist band includes elastic portions spaced apart from said splitting means.

6. The invention as defined in claim 2 wherein each said leg includes elastic portions spaced apart from said splitting means.

7. The invention as defined in claim 1 wherein said inner layer is made of paper.

8. The invention as defined in claim 1 wherein said outer layer comprises synthetic plastic material.

9. A training panty comprising;
a panty member having a waist band defining a waist opening and two leg bands defining two spaced apart leg openings separated by an intermediate portion of said member;
means for selectively splitting said member, said waist band and both said leg bands,
means for bifurcating the intermediate member portion along a first line extending from one leg opening to the other leg opening and means for bifurcating said member along a second line extending inclusively from said waist band to one of said first line and said leg opening;
wherein said means for selectively splitting comprises at least one first flap portion, at least one second flap portion and means for detachably securing said at least one first flap portion to said at least one second flap portion and wherein said at least one first flap portion overlaps said at least one second portion along said second line and further comprising at least one third flap portion and means for detachably securing said third flap portion to each of said first and second flap portions along said first line.

10. A training panty comprising;
a panty member having a waist band defining a waist opening and two leg bands defining two spaced apart leg openings separated by an intermediate portion of said member;
means for selectively splitting said member, said waist band and both said leg bands;
wherein said means for selectively splitting comprises means for bifurcating said member along a first line extending from said waist band to one of said two leg bands and means for bifurcating said member along a second line extending from said waist band to the other of said leg bands.

11. The invention as defined in claim 10 wherein each said bifurcating means comprises a first flap portion having an edge at each opposite end, a second flap portion having an edge at each opposite end, and means for detachably securing said edges of said first and second flap portion.

12. The invention as defined in claim 11 wherein said means for detachably securing comprises hook and pile fastening means for selectively securing said edges together.

13. The invention as defined in claim 10 wherein each said bifurcating means comprises;
a strand having greater cohesive strength than said member, said waist band and said leg bands, and means for securing said strand to panel member, said waist band and said leg band.

14. A training panty comprising:
a panty member having an elasticized waist opening and two leg bands defining two spaced apart leg openings separated by an intermediate portion of said panty member, said panty member being formed with an outer layer of material substantially impervious to water, and an inner layer of water absorbant material, and means for selectively separating said panty member, by separating said waist opening and both said leg bands, said means comprising means for separating said panty member along a first line extending from said waist opening to one of said two leg bands and means for separating said panty member along a second line extending from said waist opening to the other of said leg bands.

15. The invention as defined in claim 14 wherein each said bifurcating means comprises a first flap portion having an edge at each opposite end, a second flap portion having an edge at each opposite end, and means for detachably securing said edges of said first and second flap portions.

16. The invention as defined in claim 15 wherein said means for detachably securing comprises hook and pile fastening means for selectively securing said edges together.

17. The invention as defined in claim 14 wherein each said bifurcating means comprises;
a strand having greater cohesive strenth than said member, said waist band and said leg bands, and means for securing said strand to panel member, said waist band and said leg band.

* * * * *

UNITED STATES PATENT AND TRADEMARK OFFICE
CERTIFICATE OF CORRECTION

PATENT NO. : 4,610,680
DATED : September 9, 1986
INVENTOR(S) : Ruby S. La Fleur

It is certified that error appears in the above-identified patent and that said Letters Patent are hereby corrected as shown below:

Column 5, line 29, claim 6, delete "2" and insert --1--;

line 30, claim 6, after "leg" insert --band--.

Column 6, line 57, claim 17, delete "strenth" and insert

--strength--.

Signed and Sealed this

Tenth Day of February, 1987

Attest:

DONALD J. QUIGG

Attesting Officer *Commissioner of Patents and Trademarks*